United States Patent
Ishikawa et al.

(10) Patent No.: US 11,631,492 B2
(45) Date of Patent: Apr. 18, 2023

(54) HOSPITAL SUPPORT SYSTEM, HOSPITAL SUPPORT METHOD, HOSPITAL SUPPORT PROGRAM, AND CONTROL DEVICE

(71) Applicant: FUJIFILM Corporation, Tokyo (JP)

(72) Inventors: Shigetoshi Ishikawa, Kanagawa (JP); Hirona Yumbe, Kanagawa (JP); Akemi Oda, Kanagawa (JP); Yasuhisa Kaneko, Kanagawa (JP); Haruyasu Nakatsugawa, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/398,288

(22) Filed: Apr. 30, 2019

(65) Prior Publication Data

US 2019/0348172 A1  Nov. 14, 2019

(30) Foreign Application Priority Data

May 11, 2018 (JP) .............................. JP2018-092393

(51) Int. Cl.
*A61B 5/00* (2006.01)
*G06Q 10/00* (2023.01)
(Continued)

(52) U.S. Cl.
CPC .................................. *G16H 40/20* (2018.01)

(58) Field of Classification Search
CPC ..... A61B 5/681; A61B 5/0022; A61B 5/1117; A61B 5/0006; A61B 5/1112; G16H 40/67;
(Continued)

(56) References Cited

U.S. PATENT DOCUMENTS 10,347,378 B2   7/2019 Okabe et al.
2003/0060678 A1  3/2003 Watai et al.
(Continued)

FOREIGN PATENT DOCUMENTS

JP  2003061907  3/2003
JP  2004329926  11/2004
(Continued)

OTHER PUBLICATIONS

"Office Action of Japan Counterpart Application" with English translation thereof, dated Aug. 3, 2021, p. 1-p. 3.
(Continued)

*Primary Examiner* — Maroun P Kanaan
(74) *Attorney, Agent, or Firm* — JCIPRNET

(57) ABSTRACT

A hospital support system includes a management monitor and an operation terminal functioning as a first controller that performs control for displaying a status management table in a state in which items corresponding to a series of predetermined multiple stages performed so as to correspond to a diseased animal at least while the diseased animal stays in a hospital from when the diseased animal arrives at the hospital to when payment is finished are arranged in a sequence of time on the management monitor and a second controller that performs control for displaying an icon indicating which stage of the multiple stages in the status management table is a stage being performed at a current point of time on the management monitor.

18 Claims, 8 Drawing Sheets

(51) Int. Cl.
*G06Q 50/00* (2012.01)
*G16H 40/20* (2018.01)

(58) Field of Classification Search
CPC ........ G16H 50/20; G16H 20/13; G16H 80/00; G16H 15/00; G16H 20/30; G16H 40/63; G16H 10/60; G16H 40/20
See application file for complete search history.

(56) References Cited

U.S. PATENT DOCUMENTS

| | | | |
|---|---|---|---|
| 2004/0267575 A1 | 12/2004 | Boing | |
| 2013/0095459 A1* | 4/2013 | Tran | G09B 19/00 434/247 |
| 2015/0095062 A1 | 4/2015 | Sato et al. | |
| 2015/0106121 A1* | 4/2015 | Muhsin | G06F 19/00 705/3 |
| 2016/0042131 A1 | 2/2016 | Saitoh et al. | |
| 2016/0371443 A1 | 12/2016 | Kudo et al. | |
| 2017/0116373 A1* | 4/2017 | Ginsburg | G16H 40/20 |
| 2018/0107797 A1* | 4/2018 | Schuck | G06F 16/245 |

FOREIGN PATENT DOCUMENTS

| | | |
|---|---|---|
| JP | 2006338521 | 12/2006 |
| JP | 2009080676 | 4/2009 |
| JP | 2015069578 | 4/2015 |
| JP | 2015176223 | 10/2015 |
| JP | 2016038747 | 3/2016 |
| JP | 2016143205 | 8/2016 |

OTHER PUBLICATIONS

"Office Action of Japan Counterpart Application" with English translation thereof, dated Dec. 13, 2022, p. 1-p. 8.
Office Action of Japan Counterpart Application, with English translation thereof, dated Apr. 27, 2021, pp. 1-6.

* cited by examiner

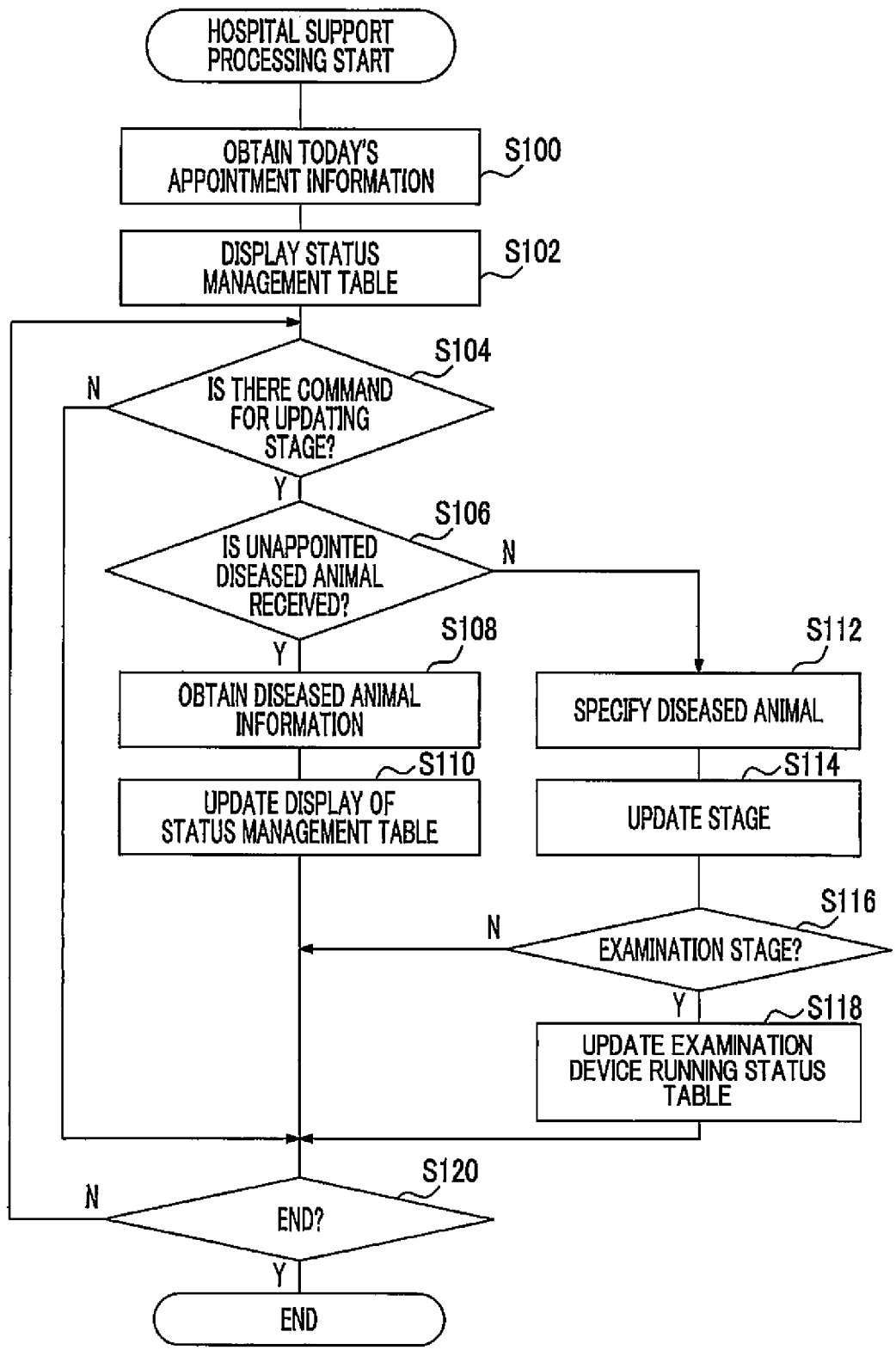

FIG. 8

| | ADMISSION/ ACCOMMODATION | RECEPTION | CHECK-UP/ TREATMENT | EXAMINATION | IN-HOSPITAL | OUT-OF-HOSPITAL | DIAGNOSIS/ TREATMENT | DISPENSING | PAYMENT | ADMISSION/ ACCOMMODATION | EXAMINATION DEVICE RUNNING STATUS |
|---|---|---|---|---|---|---|---|---|---|---|---|
| FUJI KOTARO 1234-1 13 YEARS 6 MONTHS GOLDEN RETRIEVER MALE DOG AM 09:15 | | | | | | | | | | | NAKASHIMA AZUKI [photo] NUMBER OF WAITING ANIMALS: 1 90% OF PROCESSING IN PROGRESS |
| TAIYO HANAKO 1250-1 10 YEARS 3 MONTHS CORGI FEMALE CAT AM 09:30 | | | | | | | | [photo] | [photo] | | KATO VANILLA [photo] |
| ISHIKAWA MOMO 1240-1 7 YEARS 8 MONTHS EXOTIC FEMALE CAT AM 10:00 | | | | | BLOOD GENERAL EXAMINATION | ALLERGY EXAMINATION | [photo] | | ASPIRIN TABLETS FOR SIX DAYS CAPSULE TABLETS FOR SIX DAYS | | 50% OF PROCESSING IN PROGRESS |
| NAKASHIMA AZUKI 1130-1 12 YEARS 2 MONTHS SCOTTISH FOLD FEMALE CAT AM 09:45 | | | | [photo] | URINE EXAMINATION BLOOD CHEMICAL EXAMINATION | | | | | | YUMIBE GON [photo] |
| KATO VANILLA 1230-1 10 YEARS 6 MONTHS TOY POODLE FEMALE DOG AM 09:45 | | | | [photo] | IMMUNOLOGICAL EXAMINATION BLOOD CHEMICAL EXAMINATION | | | | | | [photo] |
| YUMIBE GON 1252-1 5 YEARS 2 MONTHS FRENCH BULLDOG MALE DOG AM 10:15 | | | | [photo] | RADIATION (BRAIN PART) | | | | | | |
| ODA CHOCO 1010-1 7 YEARS 6 MONTHS RUSSIAN BLUE MALE CAT AM 10:45 | | | [photo] | | | | | | | | |
| KANEKO SAKURA 1240-1 10 YEARS 5 MONTHS MINIATURE DACHSHUND FEMALE DOG AM 11:00 | | [photo] | | | | | | | | | |
| NAKATSUGAWA SORA 1200-1 6 YEARS 6 MONTHS SHIBA MALE DOG AM 11:15 | | [photo] | | | | | | | | | |
| TSUBOTA ANKO 1263-1 10 YEARS 6 MONTHS POMERANIAN FEMALE DOG AM 11:30 | [photo] | | | | | | | | | | |

HOSPITAL SUPPORT SYSTEM, HOSPITAL SUPPORT METHOD, HOSPITAL SUPPORT PROGRAM, AND CONTROL DEVICE

CROSS-REFERENCE TO RELATED APPLICATIONS

This application claims priority from Japanese Patent Application No. 2018-092393, filed May 11, 2018, the disclosure of which is incorporated herein by reference in its entirety.

BACKGROUND

1. Technical Field

The present disclosure relates to a hospital support system, a hospital support method, a hospital support program, and a control device.

2. Related Art

In the related art, in order for a hospital staff such as a doctor, a nurse, and an engineer to recognize a check-up schedule for subjects, information on reception or payment of the subject is displayed on a display device for each subject in a hospital. For example, a technology in which an appointment time, a reception time, and an examination waiting state are displayed on the display device for each diseased animal which is the subject is described in a technology described in JP2015-069578A.

In the technology described in JP2015-069578A, it is difficult to recognize a current status of the subject in the hospital such as which stage of the series of predetermined multiple stages including a stage of the reception or examination performed for the subject is finished or which stage is a stage being performed at the current point of time. Thus, it is difficult for the staff to recognize the schedule for the subjects in the entire hospital.

The present disclosure has been made in view of the aforementioned circumstances, and an object of the present disclosure is to provide a hospital support system, a hospital support method, a hospital support program, and a control device capable of easily recognizing a schedule for subjects in the entire hospital.

SUMMARY

In order to achieve the object, a hospital support system of a first aspect of the present disclosure comprises: a display device; a first controller that performs control for displaying a table in a state in which items corresponding to a series of predetermined multiple stages performed so as to correspond to a subject at least while the subject stays in a hospital from when the subject arrives at the hospital to when payment is finished are arranged in a sequence of time on the display device; and a second controller that performs control for displaying stage information indicating which stage of the multiple stages in the table is a stage being performed at a current point of time on the display device.

In the hospital support system of the first aspect, in a hospital support system of a second aspect of the present disclosure, the second controller displays, as the stage information, an image of the subject in a position indicating the stage.

In the hospital support system of the first or second aspect, in a hospital support system of a third aspect of the present disclosure, the multiple stages further include at least one stage of a stage related to a visiting schedule for the subject, a stage related to accommodation, a stage related to admission, or a stage related to discharge.

In the hospital support system of any one of the first to third aspects, in a hospital support system of a fourth aspect of the present disclosure, the multiple stages include a stage related to a medical care of the subject and a stage related to an examination of the subject.

In the hospital support system of the fourth aspect, a hospital support system of a fifth aspect of the present disclosure further comprises: a third controller that performs control for further displaying information indicating a running status of a device used for at least one of the medical care or the examination on the display device.

In the hospital support system of the fifth aspect, in a hospital support system of a sixth aspect of the present disclosure, the information indicating the running status is information indicating at least one of a remaining time until the running of the device is finished for the medical care or the examination being performed, an end time when the running of the device is scheduled to be ended, a progress status of the running of the device for the medical care or the examination, or the number of subjects waiting for at least one of the medical care or the examination using the device.

In the hospital support system of any one of the first to sixth aspects, in a hospital support system of a seventh aspect of the present disclosure further comprises: a tag that stores identification information for identifying the subject; and a reader that is provided in a predetermined position for each stage and reads the identification information from the tag. In a case where the reader reads the identification information from the tag, the second controller updates a stage corresponding to the reader in display of the display device.

In the hospital support system of the seventh aspect, in a hospital support system of an eighth aspect of the present disclosure, the tag is attached to the subject.

In the hospital support system of any one of the first to eighth aspects, a hospital support system of a ninth aspect of the present disclosure further comprises: a storage unit that stores description information described for the subject; and a wearable device that includes a transmission unit which transmits the description information stored in the storage unit. In a case where the description information transmitted by the transmission unit of the wearable device is received, the second controller updates the stage.

In the hospital support system of any one of the first to ninth aspects, in a hospital support system of a tenth aspect of the present disclosure, the second controller performs control for displaying the stage information on the display device for each of a plurality of subjects.

In the hospital support system of any one of the first to tenths aspects, a hospital support system of an eleventh aspect of the present disclosure further comprises: another display device which is provided in a check-up room, displays at least one of a result of the medical care or a result of the examination of the subject and is different from the display device.

In the hospital support system of any one of the first to eleventh aspects, a hospital support system of a twelfth aspect of the present disclosure further comprises: another display device that is provided in a waiting room, displays a part of the information displayed on the display device, and is different from the display device.

In the hospital support system of any one of the first to twelfth aspects, in a hospital support system of a thirteenth aspect of the present disclosure, the subject is an animal other than a person.

In order to achieve the object, a hospital support method of a fourteenth aspect of the present disclosure comprises: causing a first controller to perform control for displaying a table in a state in which items corresponding to a series of predetermined multiple stages performed so as to correspond to a subject at least while the subject stays in a hospital from when the subject arrives at the hospital to when payment is finished are arranged in a sequence of time on a display device; and causing a second controller to perform control for displaying stage information indicating which stage of the multiple stages in the table is a stage being performed at a current point of time on the display device.

In order to achieve the object, a non-transitory computer-readable recording medium which stores a hospital support program of a fifteenth aspect of the present disclosure causes a computer to function as: a first controller that performs control for displaying a table in a state in which items corresponding to a series of predetermined multiple stages performed so as to correspond to a subject at least while the subject stays in a hospital from when the subject arrives at the hospital to when payment is finished are arranged in a sequence of time on a display device; and a second controller that performs control for displaying stage information indicating which stage of the multiple stages in the table is a stage being performed at a current point of time on the display device.

In order to achieve the object, a control device of a sixteenth aspect of the present disclosure comprises a first controller that performs control for displaying a table in a state in which items corresponding to a series of predetermined multiple stages performed so as to correspond to a subject at least while the subject stays in a hospital from when the subject arrives at the hospital to when payment is finished are arranged in a sequence of time on a display device; and a second controller that performs control for displaying stage information indicating which stage of the multiple stages in the table is a stage being performed at a current point of time on the display device.

According to the present disclosure, it is possible to easily recognize a schedule for subjects in the entire hospital.

BRIEF DESCRIPTION OF THE DRAWINGS

Exemplary embodiments according to the technique of the present disclosure will be described in detail based on the following figures, wherein:

FIG. 7 is a flowchart showing an example of hospital support processing performed by the operation terminal of the embodiment;

FIG. 8 is an explanatory diagram for describing examples of a status management table and an examination device running status table displayed on the management monitor of the embodiment;

DETAILED DESCRIPTION

Hereinafter, an embodiment for implementing a technology of the present disclosure will be described in detail with reference to the drawings.

Figure 1:
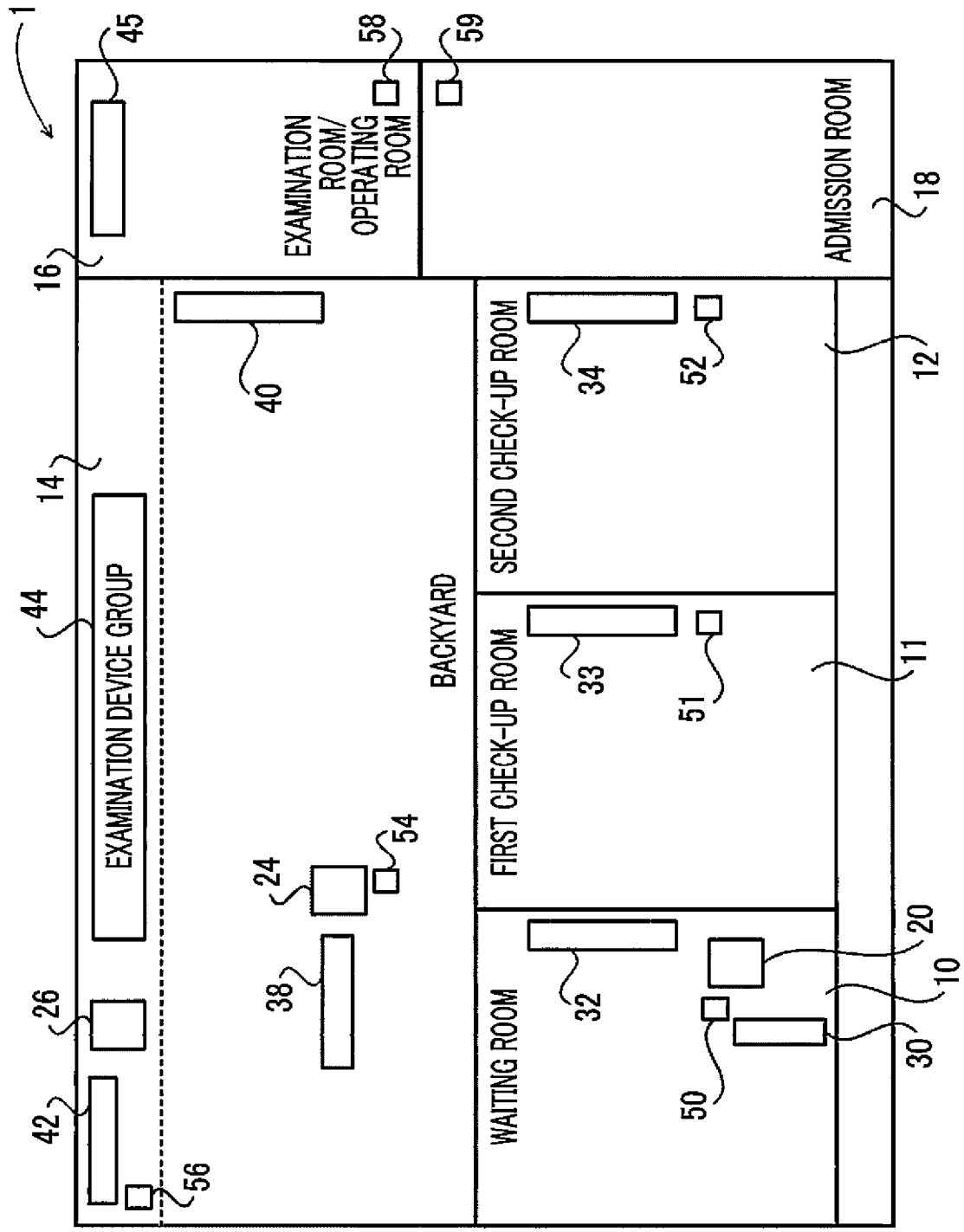
FIG. 1 is a plan view showing an example of a configuration of an animal hospital of an embodiment.

Initially, an example of an animal hospital which is a support target of a hospital support system of the present embodiment will be described with reference to FIG. 1. FIG. 1 shows a plan view of an example of the animal hospital which is the support target of the hospital support system of the present embodiment.

As shown in FIG. 1, an animal hospital 1 is provided with a waiting room 10, a first check-up room 11, a second check-up room 12, a backyard 14, an examination room/operating room 16 that serves as both an examination room and an operating room, and an admission room 18.

In the waiting room 10, a reception for receiving an animal (hereinafter, referred to a "diseased animal" regardless of morbidity) as a subject which visits the animal hospital 1 is provided, and a reception/payment terminal 20 and a reception/payment terminal monitor 30 to be used for receiving the diseased animal or payment by a staff (hereinafter, referred to as a "staff") such as a veterinarian or a nurse of the animal hospital 1 are disposed. A waiting room monitor 32 for displaying information on contents using an owner of the diseased animal who waits for a check-up as a target to be watched is disposed in the waiting room 10. The waiting room monitor 32 may be a type to display various advertisements related to the diseased animal, information useful for health care of the diseased animal (information on diseases, health diagnosis, pet food, or the like), or an introduction of the animal hospital 1 (an introduction of pet hotels or an introduction related to trimming in a case where the trimming is performed). The waiting room monitor 32 may be a type to display photographs of diseased animals. For example, the waiting room monitor displays one or a plurality of favorite photographs captured by the owner, and thus, it is possible to smoothly facilitate communication between the owners.

A check-up or treatment (curing) on the diseased animal is performed by the veterinarian in each of the first check-up room 11 and the second check-up room 12. A check-up monitor 33 for displaying information on check-up contents or information on the diseased animal such as a so-called medical chart is disposed in the first check-up room 11, and a check-up monitor 34 for the same purpose is disposed in the second check-up room 12. Results of examinations using an examination device group 44 and a radiological examination device 45, for example, a result of a blood examination, a radiographic image, and an ultrasound image are also displayed on the check-up monitor 33 and the check-up monitor 34 of the present embodiment according to a command of the staff.

An operation terminal 24, an operation input monitor 38, and a management monitor 40 are provided in the backyard 14, and the entire management of the animal hospital 1 is performed by the staff by using the operation terminal 24, the operation input monitor 38, and the management monitor 40. The operation terminal 24 of the present embodiment controls the entire hospital support system 4 (see FIG. 2) used for managing the animal hospital 1. The operation terminal 24 of the present embodiment is an example of a control device of the present disclosure. The management monitor 40 of the present embodiment is an example of a display device of the present disclosure.

The examination or treatment on the diseased animal or a specimen obtained from the diseased animal is performed by the veterinarian in the backyard 14. Thus, the examination device group 44 used in the examination, an examination management terminal 26 and an examination management monitor 42 for managing the general examination are disposed in the backyard 14. For example, the examination device group 44 includes a blood chemical examination device, an immunological examination device, a radiological examination device, and an ultrasound examination device. The examination device group is not particularly limited, and may include an endoscopic examination device. As a specific example of each of the blood chemical examination device and the immunological examination device, there is a product name "DRI-CHEM (registered trademark)" manufactured by FUJIFILM Corporation.

In the examination room/operating room 16, the imaging of the radiographic image of the diseased animal or the surgery on the diseased animal is performed by the veterinarian. The radiological examination device 45 for imaging the radiographic image of the diseased animal is disposed in the examination room/operating room 16, and the radiological examination device 45 is managed by using the examination management terminal 26 provided in the backyard 14.

A plurality of diseased animals can be admitted (accommodated) in the admission room 18, and a plurality of animals can stay in the admission room as a so-called pet hotel.

As shown in FIG. 1, a tag reader 50, a tag reader 51, a tag reader 52, tag readers 54 and 56, a tag reader 58, and a tag reader 59 as readers for reading integrated circuit (IC) tags storing identification numbers (to be described in detail) for managing the diseased animals are respectively provided in the waiting room 10, the first check-up room 11, the second check-up room 12, the backyard 14, the examination room/operating room 16, and the admission room 18. In the present embodiment, the IC tag is included in a check-up card of the diseased animal, for example.

Figure 2:
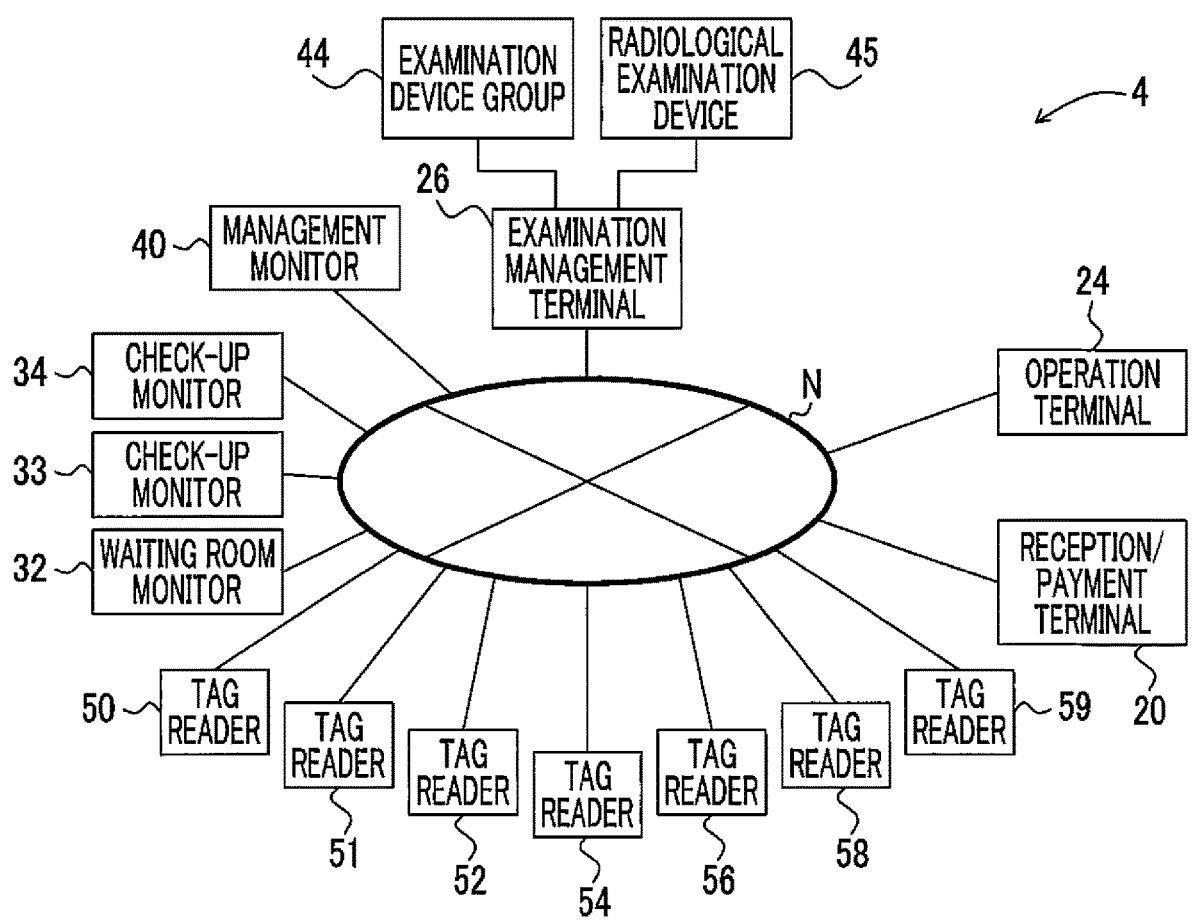
FIG. 2 is a block diagram showing an example of a configuration of a hospital support system of the embodiment.

Next, a configuration of the hospital support system 4 of the present embodiment will be described with reference to FIG. 2. As shown in FIG. 2, in the hospital support system 4 of the present embodiment, the reception/payment terminal 20, the operation terminal 24, the examination management terminal 26, the waiting room monitor 32, the check-up monitor 33, the check-up monitor 34, the management monitor 40, and the tag readers 50, 51, 52, 54, 56, 58, and 59 which are stated above are connected to an intra-hospital network N provided within the animal hospital 1 so as to enable communication. The examination management terminal 26, the examination device group 44, and the radiological examination device 45 are connected so as to enable communication without the network N. The communication between the examination management terminal 26, the examination device group 44, and the radiological examination device 45 may be performed in a wireless communication manner or in a wired communication manner.

Figure 3:
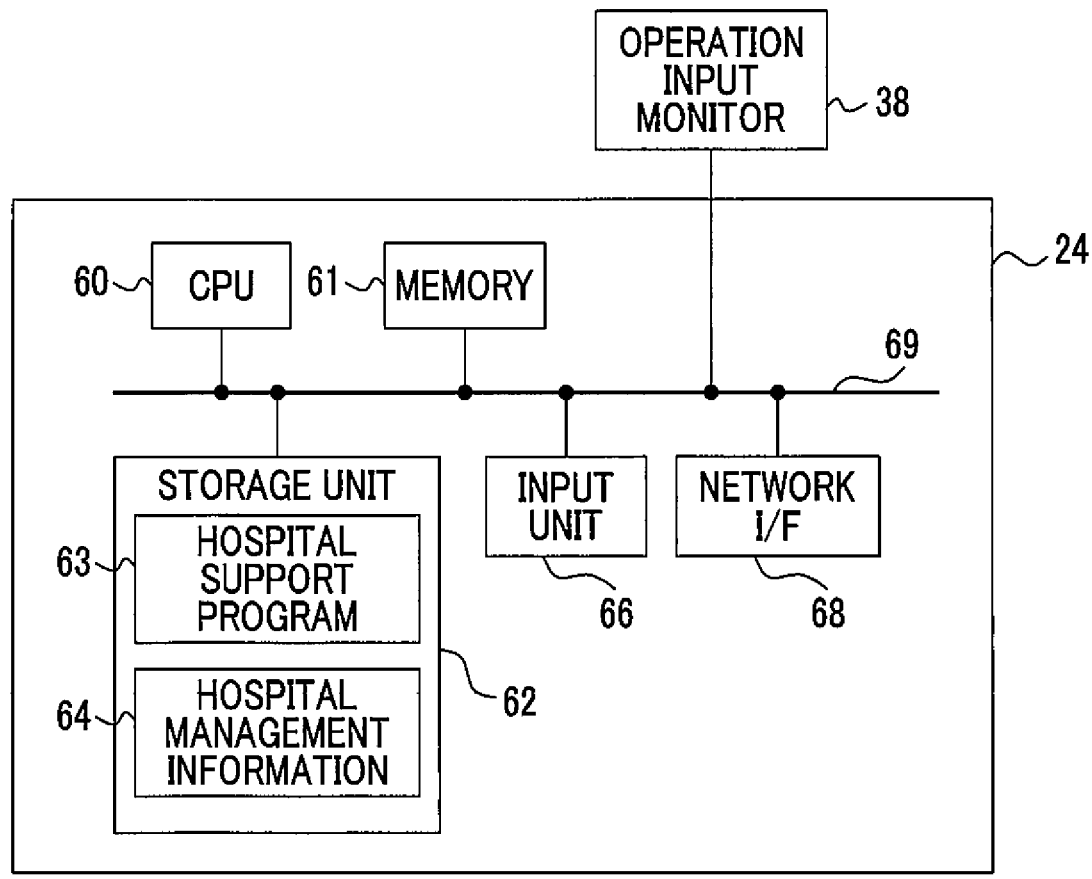
FIG. 3 is a block diagram showing an example of a hardware configuration of an operation terminal of the embodiment.

Next, a hardware configuration of the operation terminal 24 of the present embodiment will be described with reference to FIG. 3. As shown in FIG. 3, the operation terminal 24 includes a central processing unit (CPU) 60, a memory 61 as a temporary storage region, and a non-volatile storage unit 62. The operation terminal 24 includes an input unit 66 such as a keyboard or a mouse and a network interface (I/F) 68 connected to the network N. The CPU 60, the memory 61, the storage unit 62, the input unit 66, the network I/F 68, and the operation input monitor 38 are connected to a bus 69 so as to enable communication.

The storage unit 62 is realized by a hard disk drive (HDD), a solid state drive (SSD), and a flash memory. A hospital support program 63 is stored in the storage unit 62 as a storage medium. The CPU 60 reads out the hospital support program 63 from the storage unit 62, develops the readout program into the memory 61, and executes the developed hospital support program 63. Diseased animal information on the diseased animal which is recorded in a so-called medical chart or hospital management information 64 including various information for managing the entire animal hospital 1 is stored in the storage unit 62.

Figure 4:
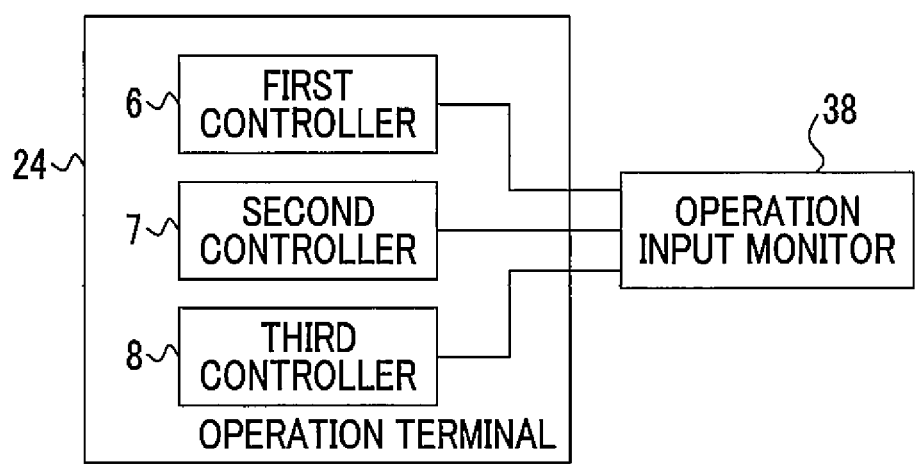
FIG. 4 is a block diagram showing an example of a functional configuration of the operation terminal of the embodiment.

A functional configuration of the operation terminal 24 of the present embodiment will be described with reference to FIG. 4. As shown in FIG. 4, the operation terminal 24 includes a first controller 6, a second controller 7, and a third controller 8. The CPU 60 executes the hospital support program 63, and thus, the operation terminal functions as the first controller 6, the second controller 7, and the third controller 8.

The first controller 6 has a function of performing control for displaying a status management table 100 (see FIG. 8) in a state in which items (to be described in detail) corresponding to the series of predetermined multiple stages performed so as to correspond to the diseased animal at least while the diseased animal stays in the animal hospital 1 from when the diseased animal arrives at the animal hospital 1 to when payment is finished are arranged in a sequence of time on the operation input monitor 38. The second controller 7 has a function of performing control for displaying stage information indicating which stage of the multiple stages in the status management table 100 is a stage being performed at a current point of time on the operation input monitor 38. The third controller 8 has a function of performing control for further displaying an examination device running status table 102 indicating running statuses of the examination device group 44 and the radiological examination device 45 on the operation input monitor 38.

Figure 5:
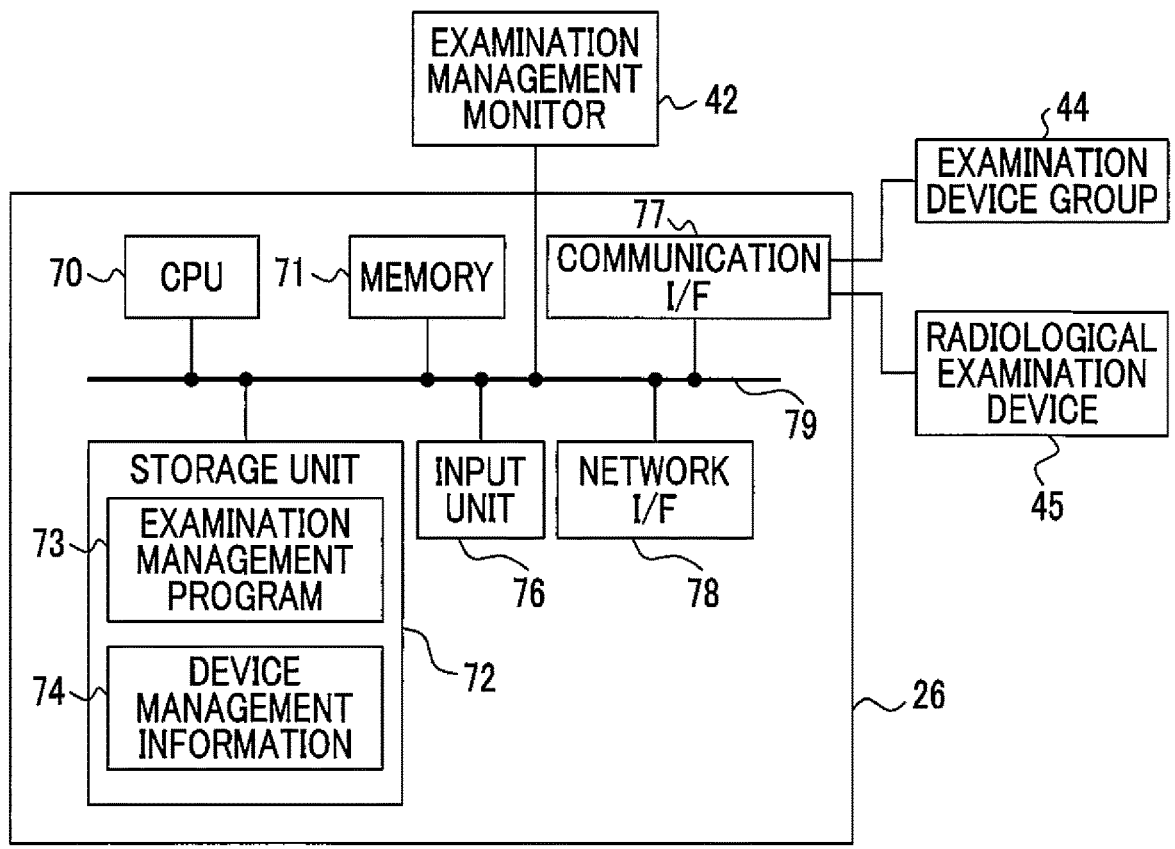
FIG. 5 is a block diagram showing an example of a hardware configuration of an examination management terminal of the embodiment.

A hardware configuration of the examination management terminal 26 of the present embodiment will be described with reference to FIG. 5. As shown in FIG. 5, the examination management terminal 26 includes a CPU 70, a memory 71 as a temporary storage region, and a non-volatile storage unit 72. The examination management terminal 26 includes an input unit 76 such as a keyboard or a mouse, a communication I/F 77 for communicating with the examination device group 44 and the radiological examination device 45, and a network I/F 78 connected to the network N. The CPU 70, the memory 71, the storage unit 72, the input unit 76, the communication I/F 77, the network I/F 78, and the examination management monitor 42 are connected to a bus 79 so as to enable communication.

The storage unit 72 is realized by an HDD, an SSD, and a flash memory. An examination management program 73 is stored in the storage unit 72 as the storage medium. The CPU 70 reads out an examination management program 73 from the storage unit 72, develops the readout program into the memory 71, and executes the developed examination management program 73. Device management information 74 for managing the examination device group 44 and the radiological examination device 45 is stored in the storage unit 72.

Figure 6:
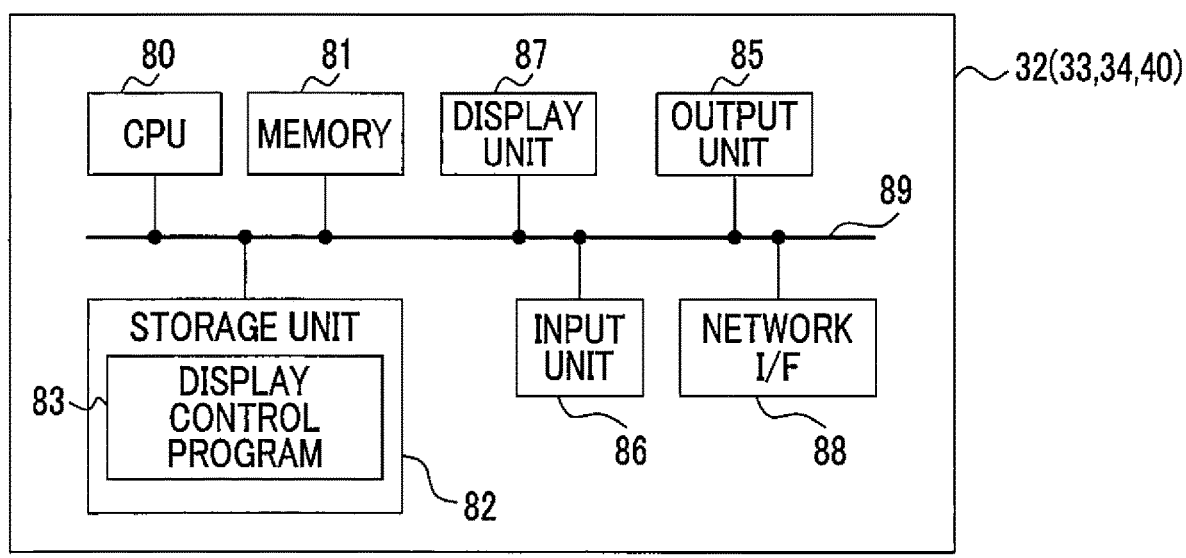
FIG. 6 is a block diagram showing an example of hardware configurations of a waiting room monitor, a check-up monitor, and a management monitor of the embodiment.

A hardware configuration of the waiting room monitor 32 of the present embodiment will be described with reference to FIG. 6. As shown in FIG. 6, the waiting room monitor 32 includes a CPU 80, a memory 81 as a temporary storage region, and a non-volatile storage unit 82. The waiting room monitor 32 includes an output unit 85 such as a speaker that outputs voice, an input unit 86 such as a remote controller, a display unit 87 such as liquid crystal display, and a network I/F 88 connected to the network N. The CPU 80, the memory 81, the storage unit 82, the output unit 85, the input unit 86, the display unit 87, and the network I/F 88 are connected to a bus 89 so as to enable communication.

The storage unit 82 is realized by an HDD, an SSD, and a flash memory. A display control program 83 is stored in the storage unit 82 as the storage medium. The CPU 80 reads out the display control program 83 from the storage unit 82, develops the readout program into the memory 81, and executes the developed display control program 83. The CPU 80 performs control for displaying various information on the display unit 87 according to the control of the operation terminal 24 by executing the display control program 83.

The hardware configurations of the check-up monitor 33, the check-up monitor 34, and the management monitor 40 are the same as that of the waiting room monitor 32, and thus, the description thereof will be omitted.

Next, the actions and effects of the hospital support system 4 of the present embodiment will be described. In the hospital support system 4 of the present embodiment, the operation terminal 24 controls the entire hospital support system 4 as stated above. In the present embodiment, the CPU 60 of the operation terminal 24 executes the hospital support program 63, and thus, hospital support processing shown in FIG. 7 is performed. For example, the hospital support processing shown in FIG. 7 is performed at a timing when a power supply (not shown) is input to the operation terminal 24.

In step S100 of FIG. 7, the CPU 60 of the operation terminal 24 obtains today's appointment information. Specifically, the CPU 60 obtains the diseased animal information on the diseased animals whose visits are appointed today while referring to the hospital management information 64.

In the next step S102, the CPU 60 generates the status management table 100 in a state in which the diseased animals whose visits are appointed are arranged in a sequence of time in the order of earlier appointment times, and displays the generated table on the management monitor 40. In the hospital support system 4 of the present embodiment, the CPU 60 of the operation terminal 24 executes the hospital support processing, and thus, the status management table 100 shown in FIG. 8 as an example is displayed on the management monitor 40.

As shown in FIG. 8, the status management table 100 is a table in a state in which the items corresponding to the series of predetermined multiple stages performed so as to correspond to the diseased animal are arranged in a sequence of time while the diseased animal stays in the animal hospital 1. The stage information indicating which stage of the multiple stages in the status management table 100 is the stage being performed at the current point of time is displayed for each diseased animal. In the present embodiment, "admission/accommodation", "reception", "check-up/treatment", "examination", "diagnosis/treatment", "dispensing", "payment", and "admission/accommodation" in a sequence of time are adopted as examples of the predetermined multiple stages, and the items corresponding to the stages are displayed on the status management table 100 while being arranged in a sequence of time. Among these stages, the stage of "admission/accommodation" is an example of a stage related to a visiting schedule, a stage related to accommodation, a stage related to admission, and a stage related to discharge in the present disclosure. The stages of "reception", "check-up/treatment", "diagnosis/treatment", and "dispensing" are examples of stages related to medical care of the present disclosure, and "examination" is an example of a stage related to the examination of the subject of the present disclosure.

In the status management table 100, an icon 100B indicating the diseased animal is displayed in a position of the stage at the current point of time of each diseased animal. Thus, in the status management table 100 shown in FIG. 8, the icon 100B of the diseased animal move to the right direction as the stage proceeds. As a specific example of the icon 100B of the diseased animal, there is an icon using a photograph of the diseased animal. In a case where the photograph of the diseased animal is used, data on the photograph of the diseased animal provided by the owner of the diseased animal may be used. In this case, the data on the photograph of the diseased animal is electronically provided to the hospital support system 4, and thus, contact information such as a mail address of the owner can be obtained. Accordingly, it is possible to use the obtained contact information for contacting the owner from the animal hospital 1 or contracting the owner about an examination result of the diseased animal.

Figure 9:
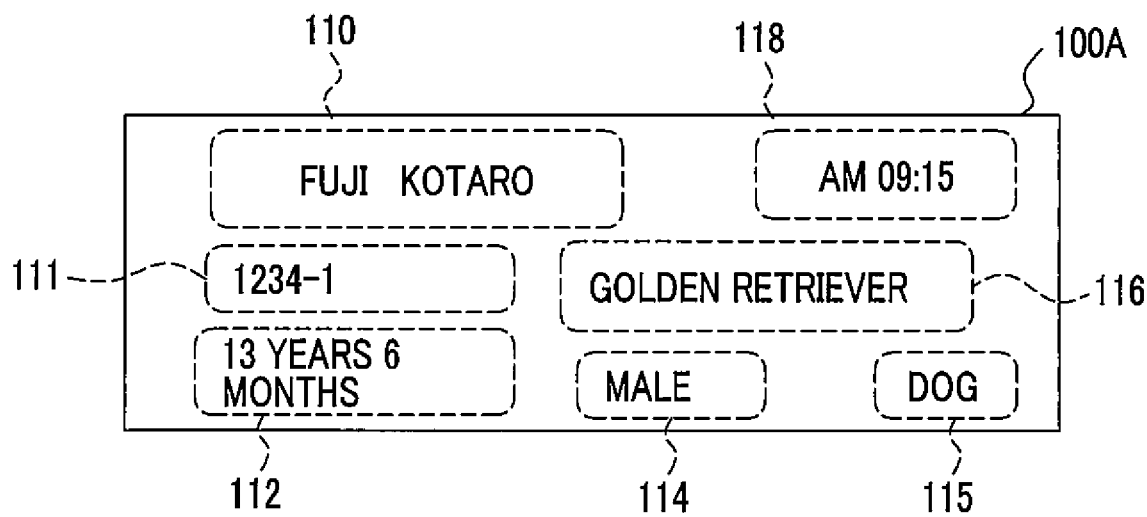
FIG. 9 is an explanatory diagram for describing information displayed in the status management table of the embodiment.

The status management table 100 includes display of information 100A which is a part of the diseased animal information for each diseased animal. In the present embodiment, examples of the information 100A include a name 110 of the diseased animal, an identification number 111, an age 112, a gender 114, a type 115, a breed 116, and an appointment time 118, as shown in FIG. 9. In a case where the reception of the diseased animal is finished and the stage at the current point of time is "reception", the appointment time 118 is changed to a reception time.

In the next step S104, the CPU 60 determines whether or not a command for updating the stage is received. In the present embodiment, in a case where identification information is read from the IC tag, each of the tag readers 50, 51, 52, 54, 56, 58, and 59 transmits the identification information to the operation terminal 24, and transmits a command for updating the stage of the diseased animal at the current point of time. In a case where the command for updating the stage is received, the CPU 60 updates the stage corresponding to any of the tag readers 50, 51, 52, 54, 56, 58, and 59 as transmission sources for the diseased animal corresponding to the received identification information.

In a case where the command for updating the stage is not received from any of the tag readers 50, 51, 52, 54, 56, 58, and 59 through the network I/F 68, the determination in step S104 is a negative determination, and the CPU proceeds to step S120. Meanwhile, in a case where the command for updating the stage is received from any one of the tag readers 50, 51, 52, 54, 56, 58, and 59 through the network I/F 68, the determination in step S104 is a positive determination, and the CPU proceeds to step S106.

In step S106, the CPU 60 determines whether or not an unappointed diseased animal is received. Specifically, in a case where an identification number different from an identification number of the diseased animal included in the today's appointment information obtained in step S100 is received from the tag reader 50, the CPU 60 determines that the unappointed diseased animal is received. In a case where the unappointed diseased animal is received, the determination in step S106 is a positive determination, and the CPU proceeds to step S108.

In step S108, the CPU 60 obtains diseased animal information corresponding to the information 100A, which corresponds to the identification information received from the tag reader 50, from the hospital management information 64 stored in the storage unit 62 of the operation terminal 24. In a case where a diseased animal newly visits the animal hospital 1, the staff stores diseased animal information on the diseased animal that visits the animal hospital as the hospital management information 64 in the storage unit 62 by using the reception/payment terminal 20 or the operation terminal 24.

In the next step S110, the CPU 60 updates the status management table 100 displayed on the management monitor 40 while also including the display of the information 100A of the unappointed diseased animal, and proceeds to step S120.

Meanwhile, in a case where the unappointed diseased animal is not received, the determination in step S106 is a negative determination, and the CPU proceeds to step S112.

In step S112, the CPU 60 specifies the diseased animal based on the identification signal received from any of the tag readers 50, 51, 52, 54, 56, 58, and 59.

In the next step S114, the CPU 60 updates the display of the stage at the current point of time of the diseased animal specified in step S112 on the status management table 100 to the stage corresponding to any of the tag readers 50, 51, 52, 54, 56, 58, and 59.

Specifically, in a case where the diseased animal (and the owner) having the check-up card visits the animal hospital 1, reception processing is initially performed by the staff by using the reception/payment terminal 20. In a case where the reception is performed, the IC tag included in the check-up card is read by the tag reader 50 disposed in the waiting room 10, and an identification signal is transmitted from the tag reader 50. Thus, in a case where the identification signal is received from the tag reader 50, the CPU 60 displays the icon 100B of the diseased animal in a position corresponding to "reception" of the status management table 100 in order to display the stage at the current point of time of the diseased animal as the stage of "reception".

In a case where the medical care of the diseased animal being admitted or accommodated in the admission room 18 of the animal hospital 1 from the previous day is appointed, the icon 100B of the diseased animal is displayed in the position corresponding to "admission/accommodation" as the previous stage of "reception". Thereafter, in a case where the reception processing is performed by the owner, the icon 100B moves to the stage of "reception".

In a case where the reception is finished and the check-up is performed by the veterinarian in the first check-up room 11, the IC tag included in the check-up card is read by the tag reader 51 disposed in the first check-up room 11, and an identification signal from the tag reader 51 is transmitted. In a case where the check-up is performed by the veterinarian in the second check-up room 12, the IC tag included in the check-up card is similarly read by the tag reader 52 disposed in the second check-up room 12, and an identification signal from the tag reader 52 is transmitted. Thus, in a case where the identification signal is received from the tag reader 51 or the tag reader 52, the CPU 60 moves the icon 100B of the diseased animal in the position corresponding to the "check-up/treatment" which is the subsequent stage of "reception" in the status management table 100 in order to display the stage at the current point of time of the diseased animal as the stage of "check-up/treatment". The CPU 60 may determine whether or not the identification signal is received from any one of the tag reader 51 and the tag reader 52, and may display information indicating that the check-up is performed in any of the first check-up room 11 and the second check-up room 12 in the status management table 100.

In a case where the examination of the diseased animal or the specimen obtained from the diseased animal is performed (hereinafter, referred to as the "examination on the diseased animal") after the check-up, the IC tag included in the check-up card is read by the tag reader 56 disposed in backyard 14 or the tag reader 58 disposed in the examination room/operating room 16, and an identification signal is transmitted from the tag reader 56 or the tag reader 58. Thus, in a case where the identification signal is received from the tag reader 56 or the tag reader 58, the CPU 60 displays the icon 100B of the diseased animal in the position corresponding to "examination" which is the subsequent stage of "check-up/treatment" in the status management table 100 in order to display the stage of the diseased animal at the current point of time as the stage of "examination" in the status management table 100. In the present embodiment, in a case where the examination on the diseased animal is performed, the management of the entire examination is performed by the examination management terminal 26 as stated above. As in the example of the status management table 100 shown in FIG. 8, it is preferable that the CPU 60 obtains information indicating examination contents from the examination management terminal 26 and displays the obtained information. The example of the status management table 100 shown in FIG. 8 shows a state in which information (see "in-hospital") indicating contents of the examination performed in the animal hospital 1 and information (see "out-of-hospital") indicating contents of the examination performed out of the animal hospital 1 are displayed in line with the stage of "examination". As stated above, in a case where the information indicating the contents of the examination is displayed and the contents of the plurality of examinations is displayed, it is preferable that contents of an examination which is already finished and contents of an examination which is not finished yet are displayed so as to be easily recognized by the staff. In a case where the examination is performed out of the animal hospital 1, a request for examination to an external examination organization may be finished instead of finishing the examination. It is preferable that the required amount of specimen is also displayed according to the contents, kind, and number of "examination".

In a case where the diagnosis or treatment is performed by the veterinarian in the first check-up room 11 after the examination on the diseased animal, the IC tag included in the check-up card is read by the tag reader 51 disposed in the first check-up room 11, and the identification signal is transmitted from the tag reader 51. In a case where the diagnosis or treatment is performed by the veterinarian in the second check-up room 12, the IC tag included in the check-up card is similarly read by the tag reader 52 disposed in the second check-up room 12, and the identification signal is transmitted from the tag reader 52. Thus, in a case where the identification signal is received from the tag reader 51 or the tag reader 52, the CPU 60 moves the icon 100B of the diseased animal in the position corresponding to the "diagnosis/treatment" of the subsequent stage of "examination" in the status management table 100 in order to display the stage at the current point of time of the diseased animal as the stage of "diagnosis/treatment". The CPU 60 may determine whether or not the identification signal is received from any of the tag reader 51 or the tag reader 52, and may display information indicating which of the first check-up room 11 and the second check-up room 12 in which the diagnosis or treatment is performed is in the status management table 100.

In a case where the diagnosis or treatment is finished and dispensing is performed, the IC tag included in the check-up card is read by the tag reader 54 disposed in the backyard 14, and an identification signal is transmitted from the tag reader 54. Thus, in a case where the identification signal is received from the tag reader 54, the CPU 60 moves the icon 100B of the diseased animal in the position corresponding to "dispensing" which is the subsequent stage of "diagnosis/treatment" in the status management table 100 in order to display the stage at the current point of time of the diseased animal as the stage of "dispensing". In the present embodiment, in a case where medicine to be given to the diseased animal is dispensed, the management of dispensed contents is performed by the operation terminal 24. As in the example of the status management table 100 shown in FIG. 8, it is preferable that the CPU 60 obtains information indicating the dispensed contents from the operation terminal 24 and displays the obtained information. The example of the status management table 100 shown in FIG. 8 illustrates a state in which the information indicating the dispensed contents are displayed in line with the stage of "dispensing".

In a state in which the dispensed medicine is transferred to the owner of the diseased animal, payment processing related to the medical care is performed by the staff by using the reception/payment terminal 20. In a case where the payment is performed, the IC tag included in the check-up card is read by the tag reader 50 disposed in the waiting room 10, and an identification signal is transmitted to the tag reader 50. Thus, in a case where the identification signal is received from the tag reader 50, the CPU 60 displays the icon 100B of the diseased animal in the position corresponding to "payment" which is the subsequent stage of "dispensing" in the status management table 100 in order to display the stage at the current point of time of the diseased animal as the stage of "payment".

Thereafter, in a case where the diseased animal is admitted, the diseased animal together with the check-up card moves to the admission room 18, the IC tag included in the check-up card is read by the tag reader 59 disposed in the admission room 18, and an identification signal is transmitted from the tag reader 59. Thus, in a case where the identification signal is received from the tag reader 59, the CPU 60 displays the icon 100B of the diseased animal in the position corresponding to "admission/accommodation" which is the subsequent stage of "payment" in the status management table 100 in order to display the stage at the current point of time of the diseased animal as the stage of "admission/accommodation".

As stated above, in a case where the display of the stage at the current point of time of the diseased animal is updated, in the next step S116, the CPU 60 determines whether or not the stage at the current point of time is the stage of "examination". In a case where the stage at the current point of time is the stage other than the stage of "examination", the determination in step S116 is a negative determination, and the CPU proceeds to step S120. Meanwhile, in a case where the stage at the current point of time is the stage of "examination", the determination in step S116 is a positive determination, and the CPU proceeds to step S118.

In step S118, the CPU 60 updates the examination device running status table 102 displayed on the management monitor 40 in order to display the running status of the examination device at the current point of time, and proceeds to step S120.

As in the example shown in FIG. 8, in the hospital support system 4 of the present embodiment, the examination device running status table 102 together with the status management table 100 is also displayed on the management monitor 40. The examination device running status table 102 is a table in which information indicating the running statuses of the examination device group 44 and the radiological examination device 45 managed by the examination management terminal 26 is displayed as a display list of pictures.

Figure 10:
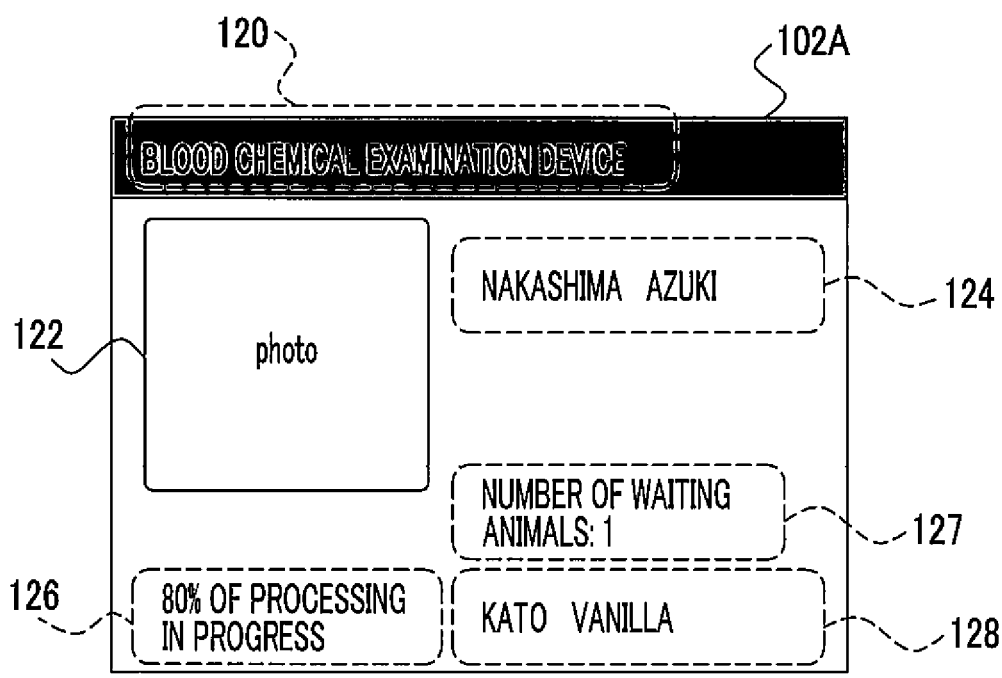
FIG. 10 is an explanatory diagram for describing information displayed in the examination device running status table of the embodiment.

The examination device running status table 102 includes display of information 102A indicating the running status of each of examination devices included in the examination device group 44 and the radiological examination device 45. As shown in FIG. 10, in the present embodiment, the information 102A includes, for example, a name 120 of the examination device, a photograph 122 of the examination device, a name 124 of the diseased animal being examined by the examination device, a running progress status 126 for examination, the number of diseased animals 127 waiting for the examination, a name 128 of the diseased animal waiting for the examination. It has been described in the example shown in FIG. 10 that information indicating what percentage of the entire processing is performed is displayed as the progress status 126, the present embodiment is not limited to this example. For example, a remaining time until the running of the examination device is finished or a scheduled timing when the running of the device is scheduled to be ended may be displayed. The CPU may perform control for displaying the progress status 126 on the waiting room monitor 32 disposed in the waiting room 10. In a case where the number of diseased animal 127 waiting for the examination exceeds to a predetermined number, the CPU may perform control for displaying information indicating that the examination is crowded on the waiting room monitor 32 disposed in the waiting room 10.

In the present embodiment, in a case where the examination is started by the examination device group 44 or the radiological examination device 45, the display contents of the examination device running status table 102 displayed on the management monitor 40 are controlled according to a command of the examination management terminal 26. For example, the progress status 126 is updated by the control of the examination management terminal 26 until the examination is finished.

The information displayed in the examination device running status table 102 is not limited to the information illustrated in the present embodiment. For example, the information displayed in the examination device running status table may be information indicating the number of remaining consumable components in each examination device of the examination device group 44 and the radiological examination device 45.

For example, in a case where the name 120 of the examination device is selected by the staff by using the input unit 86 of the management monitor 40, the examination management terminal 26 may display various information on the selected examination device as the information 102A. Examples of various information in this case include the number of remaining consumable components, information on an occurred abnormality in a case where the abnormality occurs in the examination device, or contact information such as a person who performs maintenance on the examination device.

In a case where the determination in step S104 or S116 is the negative determination, the CPU 60 determines whether or not to end the present hospital support processing in step S120 subsequent to S118. For example, until a switch (not shown) of the operation terminal 24 is turned off, the determination in step S120 is a negative determination, and the CPU returns to step S104 and repeats the processing in step S106 to S118. Meanwhile, for example, in a case where the switch of the operation terminal 24 is turned off, the determination in step S120 is a positive determination, and the present hospital support processing is ended.

As described above, the hospital support system 4 of the present embodiment comprises the management monitor 40, and the operation terminal 24 functioning as the first controller that displays the status management table 100 in a state in which the items corresponding to the series of predetermined multiple stages performed so as to correspond to the diseased animal at least while the diseased animal stays in the hospital from when the diseased animal arrives at the hospital to when the payment is finished are arranged in the sequence of time on the management monitor 40 and the second controller that performs the control for displaying the icon 100B indicating which stage of the multiple stages in the status management table 100 is the stage being performed at the current point of time on the management monitor 40.

As stated above, in the hospital support system 4 of the present embodiment, the status management table 100 is displayed on the management monitor 40 so as to easily understand which stage of the series of predetermined multiple stages performed so as to correspond to the diseased animal is the stage of the diseased animal at the current point of time. Therefore, according to the hospital support system 4 of the present embodiment, the staff of the animal hospital 1 can easily recognize a schedule for the diseased animals in the entire animal hospital 1.

Although it has been described in the present embodiment that the IC tag is included in the check-up card, the IC tag may be provided separately from the check-up card. For example, the IC tag may be provided so as to be attachable on the diseased animal, specifically, so as to be attachable on a collar of the diseased animal.

A tag having the Global Positioning System (GPS) therein may be used instead of the IC tag. In this case, in a case where the reception is performed in the animal hospital 1, the tag having the GPS therein may be attached to the diseased animal, and the operation terminal 24 may perform control for displaying a stage (for example, the current stage is the stage of "check-up/treatment" in a case where the position of the diseased animal is the first check-up room 11) corresponding to the position of the diseased animal as the current stage based on positional information of the diseased animal transmitted from the tag having the GPS therein.

Figure 11:
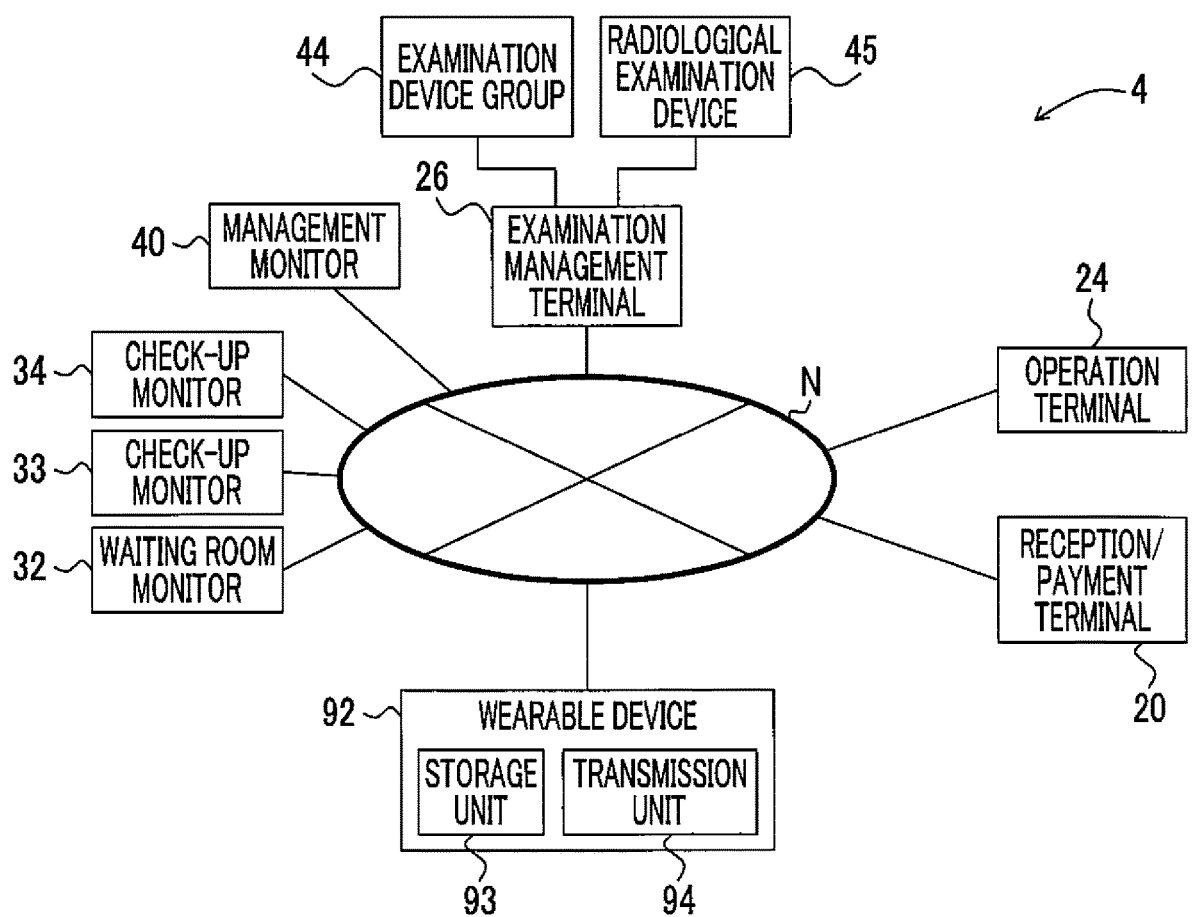
FIG. 11 is a block diagram showing another example of the configuration of the hospital support system of the embodiment.

It has been described that the stage at the current point of time of the diseased animal is updated by using the IC tag and tag readers 50, 51, 52, 54, 56, 58, and 59. However, instead of or in addition to this example, the stage at the current point of time of the diseased animal may be used in a case where predetermined information is received by the operation terminal 24 from a wearable device used by the staff or the owner of the diseased animal. An example of the configuration of the hospital support system 4 in this case is shown in FIG. 11. A wearable device 92 comprises a storage unit 93 that stores information on description on the diseased animal, such as description in the medical chart of the diseased animal, and a transmission unit 94 that transmits the information stored in the storage unit 93, and is connected to the network N so as to enable communication. As a specific example of the wearable device 92, there are a so-called electronic pen, a camera attachable to eyeglasses worn by the staff, and a camera integrated with eyeglasses.

Although it has been described in the present embodiment that the status management table 100 and the examination device running status table 102 are displayed on the management monitor 40, other information while switching to at least one of the status management table 100 or the examination device running status table 102 or together with the status management table 100 and the examination device running status table 102 may be displayed on the management monitor 40. For example, in a case where the staff designates the icon 100B in the status management table 100 by using the input unit 86 of the management monitor 40, information on the past examination results of the diseased animal corresponding to the designated icon 100B or detailed diseased animal information may be displayed on the management monitor 40.

It has been described in the present embodiment that the status management table 100 and the examination device running status table 102 are displayed on the management monitor 40. At least one of the status management table 100 or the examination device running status table 102 may be displayed on other display devices (the waiting room monitor 32, the check-up monitor 33, the check-up monitor 34, the operation input monitor 38, and the examination management monitor 42). For example, in a case where the status management table 100 is displayed on the check-up monitor 33, the diseased animal may be selected from the status management table 100, and the results of the examinations using the examination device group 44 and the radiological examination device 45, specifically, the result of the blood examination or the radiographic image, and the ultrasound image may be displayed for describing the check-up to the owner. In a case where the contents are displayed on a display device other than the management monitor 40, it is preferable that contents to be displayed are controlled according to a display device on which the contents are displayed or a place in which the display device is disposed.

Particularly, since the waiting room monitor 32 is watched by a person other than the staff of the animal hospital 1, in a case where the status management table 100 is displayed on the waiting room monitor 32, it is preferable that detailed examination contents or dispensing contents, and information on personal information of the owner or the diseased animal are not displayed. Thus, information indicating the stage at the current point of time of each diseased animal may be displayed on the waiting room monitor 32, and it is preferable that only information on a part of the status management table 100 is displayed. As stated above, it is preferable that the information indicating the stage at the current point of time of each diseased animal is displayed as a part of the status management table 100 on the waiting room monitor 32 in order for the owner who waits for in the waiting room 10 to check the current status. For example, since such display is performed, even in a case where the check-up or examination is crowded, the owner can recognize how much the check-up or examination is crowded or a rough estimate of the waiting time.

As stated above, in a case where the contents are displayed on the display device other than the management monitor 40, in a case where the contents to be displayed are controlled according to the display device on which the contents are displayed or the place in which the display device is disposed, a person stays in a range in which the display on the display device can be watched may be captured, face recognition processing may be performed on the captured image, it may be determined whether or not there is the staff of the animal hospital 1, and the contents to be displayed may be changed between a case where there is only the staff and a case where there is a person other than the staff.

Although it has been described in the present embodiment that the animal hospital 1 in which the medical care is performed on the animal other than the person is used as an example of the hospital to which the hospital support system 4 is applied and the animal (diseased animal) other than the person is used as the subject, the present invention is not limited to the present embodiment. The hospital in which the medical care is performed on the person may be used as the example of the hospital to which the hospital support system 4 is applied, and the person may be used as the subject.

Various processing performed by the CPU executing the software (program) in the aforementioned embodiment may be performed by various processors other the CPU. As the processor in this case, there are a programmable logic device (PLD) capable of changing a circuit configuration after Field-Programmable Gate Array (FPGA) is manufactured and a dedicated electric circuit which is a processor having a circuit configuration designed as a dedicated circuit in order to perform specific processing such as an Application Specific Integrated Circuit (ASIC). The various processing may be performed by one of the various processors, or may be performed by a combination of the same kind or different kinds of two or more processors (for example, a plurality of FPGAs, and a combination of the CPU and the FPGA). More specifically, the hardware configurations of the various processors are electric circuits in which circuit elements such as semiconductor elements are combined.

Although it has been described in the aforementioned embodiment that the hospital support program 63 is stored (installed) in the storage unit 62 in advance, the examination management program 73 is stored in the storage unit 72 in advance, and the display control program 83 is stored in the storage unit 82 in advance, the present invention is not limited thereto. Each of the hospital support program 63, the examination management program 73, and the display control program 83 may be stored in a recording medium such as a compact disk read only memory (CD-ROM), a digital versatile disk read only memory (DVD-ROM), and universal serial bus (USB) memory. Each of the hospital support program 63, the examination management program 73, and the display control program 83 may be downloaded from an external device through a network.

What is claimed is:

1. A hospital support system comprising:
a display device;
a tag that store identification information for identifying each subject;
a reader that is provided at a predetermined position for each of a plurality of stages scheduled in a series, that reads the identification information from the tag, and that transmits the identification information to an operation terminal;
the operation terminal comprising a processor, configured to:
obtain appointment information of each of a plurality of appointed subjects of a current day;
generate and display a table according to the appointment information of the appointed subjects in a sequence of appointed time on the display device;
in response to a first tag of a first subject among the appointed subjects being read by a first reader, provided at a first predetermined position for a first stage, among the readers and first identification information of the first tag being received from the first reader, update and display the table in a state in which items corresponding to the series of scheduled stages performed based on the first identification information of the first subject read by the first reader at the first predetermined position for the first stage at least while the first subject stays in a hospital from when the first subject arrives at the hospital to when payment is finished are arranged in a sequence of time on the display device;
display stage information indicating which stage of the scheduled stages in the table is a stage being performed at a current point of time on the display device for each of the appointed subjects, wherein the stage information comprises the first subject being at the first predetermined position for the first stage and a second subject among the appointed subjects being at the first predetermined position for the first stage; and
display information indicating a running status of a first examination device being used by the first subject at the first predetermined position and the number of waiting subjects among the appointed subjects waiting for the first examination device at the current point of time on the display, wherein the second subject is one of the waiting subjects for the first examination device.

2. The hospital support system according to claim 1, wherein the processor displays, as the stage information, an image of the first subject at the first predetermined position indicating the first stage.

3. The hospital support system according to claim 1, wherein the scheduled stages further include at least one stage of a stage related to a visiting schedule for the first subject, a stage related to accommodation, a stage related to admission, or a stage related to discharge.

4. The hospital support system according to claim 1, wherein the scheduled stages include a stage related to a medical care of the first subject and a stage related to an examination of the first subject.

5. The hospital support system according to claim 4, wherein the processor is further configured to:
perform control for further displaying information indicating a running status of a device used for at least one of the medical care or the examination on the display device.

6. The hospital support system according to claim 5, wherein the information indicating the running status is information indicating at least one of a remaining time until the running of the device is finished for the medical care or the examination being performed, an end time when the running of the device is scheduled to be ended, a progress status of the running of the device for the medical care or the examination, or the number of subjects waiting for at least one of the medical care or the examination using the device.

7. The hospital support system according to claim 1, wherein the tag is attached to the first subject.

8. The hospital support system according to claim 1, further comprising:
a memory that stores description information described for the first subject; and
a wearable device that includes a transmitter which transmits the description information stored in the memory, wherein, in a case where the description information transmitted by the transmitter of the wearable device is received, the processor updates the stage.

9. The hospital support system according to claim 1, wherein the processor performs control for displaying the stage information on the display device for each of a plurality of subjects.

10. The hospital support system according to claim 1, further comprising:
a second display device which is provided in a check-up room, and displays at least one of a result of the medical care or a result of the examination of the first subject and is different from the display device.

11. The hospital support system according to claim 1, further comprising:
a third display device that is provided in a waiting room, displays a part of the information displayed on the display device, and is different from the display device.

12. The hospital support system according to claim 1, wherein the first subject is an animal other than a person.

13. The hospital support system according to claim 1, wherein the information displayed for the first examination device comprises a percentage of the first stage having been performed for the first subject.

14. The hospital support system according to claim 1, wherein the information displayed for the first examination device comprises a remaining time until a running of the first examination device is finished by the first subject.

15. The hospital support system according to claim 1, wherein the information displayed for the first examination device further comprises a notification indicating that the first predetermined position is crowded when the number of waiting subjects waiting for the first examination device at the current point of time exceeds a predetermined threshold.

16. A hospital support method comprising:
storing identification information for identifying each subject in a tag;
providing a reader at a predetermined position for each of a plurality of stages scheduled in a series, that reads the identification information from the tag, and that transmits the identification information to an operation terminal;
obtaining, by the operation terminal, appointment information of each of a plurality of appointed subjects of a current day;
generating and displaying, by the operation terminal, a table according to the appointment information of the appointed subjects in a sequence of appointed time on a display device;
in response to a first tag of a first subject among the appointed subjects being read by a first reader, provided at a first predetermined position for a first stage, among the readers and first identification information of the first tag being received from the first reader, updating and displaying, by the operation terminal, the table in a state in which items corresponding to the series of scheduled stages performed based on the first identification information of the first subject read by the first reader at the first predetermined position for the first stage at least while the first subject stays in a hospital from when the first subject arrives at the hospital to when payment is finished are arranged in a sequence of time on a display device;
displaying, by the operation terminal, stage information indicating which stage of the scheduled stages in the table is a stage being performed at a current point of time on the display device for each of the appointed subjects, wherein the stage information comprises the first subject being at the first predetermined position for the first stage and a second subject among the appointed subjects being at the first predetermined position for the first stage; and
displaying information indicating a running status of a first examination device being used by the first subject at the first predetermined position and the number of waiting subjects among the appointed subjects waiting for the first examination device at the current point of time on the display, wherein the second subject is one of the waiting subjects for the first examination device.

17. A non-transitory computer-readable recording medium which stores a hospital support program causing a computer to:
receive identification information stored in a tag for identifying each subject from a reader that is provided at a predetermined position for each of a plurality of stages scheduled in a series and that reads the identification info nation from the tag;
obtain appointment information of each of a plurality of appointed subjects of a current day;
generate and display a table according to the appointment information of the appointed subjects in a sequence of appointed time on a display device;
in response to a first tag of a first subject among the appointed subjects being read by a first reader, provided at a first predetermined position for a first stage, among the readers and first identification information of the first tag being received from the first reader, update and display the table in a state in which items corresponding to the series of scheduled stages performed based on the first identification information of the first subject read by the first reader at the first predetermined position for the first stage at least while the first subject stays in a hospital from when the first subject arrives at the hospital to when payment is finished are arranged in a sequence of time on a display device; and
display stage information indicating which stage of the scheduled stages in the table is a stage being performed at a current point of time on the display device for each of the appointed subjects, wherein the stage information comprises the first subject being at the first predetermined position for the first stage and a second subject among the appointed subjects being at the first predetermined position for the first stage; and
display information indicating a running status of a first examination device being used by the first subject at the first predetermined position and the number of waiting subjects among the appointed subjects waiting for the first examination device at the current point of time on the display, wherein the second subject is one of the waiting subjects for the first examination device.

18. A control device comprising:

a processor, configured to:

receive identification information stored in a tag for identifying each subject from a reader that is provided at a predetermined position for each of a plurality of stages scheduled in a series and that reads the identification information from the tag;

obtain appointment information of each of a plurality of appointed subjects of a current day;

generate and display a table according to the appointment information of the appointed subjects in a sequence of appointed time on a display device;

in response to a first tag of a first subject among the appointed subjects being read by a first reader, provided at a first predetermined position for a first stage, among the readers and first identification information of the first tag being received from the first reader, update and display the table in a state in which items corresponding to the series of scheduled stages performed based on the first identification information of the first subject read by the first reader at the first predetermined position for the first stage at least while the first subject stays in a hospital from when the first subject arrives at the hospital to when payment is finished are arranged in a sequence of time on a display device;

display stage information indicating which stage of the scheduled stages in the table is a stage being performed at a current point of time on the display device for each of the appointed subjects, wherein the stage information comprises the first subject being at the first predetermined position for the first stage and a second subject among the appointed subjects being at the first predetermined position for the first stage; and display information indicating a running status of a first examination device being used by the first subject at the first predetermined position and the number of waiting subjects among the appointed subjects waiting for the first examination device at the current point of time on the display, wherein the second subject is one of the waiting subjects for the first examination device.

* * * * *